(12) United States Patent
Valla

(10) Patent No.: US 10,295,549 B2
(45) Date of Patent: May 21, 2019

(54) DIAGNOSTIC DEVICES AND METHODS OF USE

(71) Applicant: Dignity Health, Phoenix, AZ (US)

(72) Inventor: Jonathan E. Valla, Phoenix, AZ (US)

(73) Assignee: DIGNITY HEALTH, San Francisco, CA (US)

( * ) Notice: Subject to any disclaimer, the term of this patent is extended or adjusted under 35 U.S.C. 154(b) by 217 days.

(21) Appl. No.: 15/254,146

(22) Filed: Sep. 1, 2016

(65) Prior Publication Data

US 2017/0089925 A1 Mar. 30, 2017

Related U.S. Application Data

(63) Continuation of application No. 13/203,333, filed as application No. PCT/US2010/025964 on Mar. 2, 2010, now Pat. No. 9,463,458.

(60) Provisional application No. 61/156,717, filed on Mar. 2, 2009, provisional application No. 61/156,734, filed on Mar. 2, 2009.

(51) Int. Cl.
*G01N 33/68* (2006.01)
*B01L 3/00* (2006.01)

(52) U.S. Cl.
CPC ........ *G01N 33/6896* (2013.01); *B01L 3/5021* (2013.01); *B01L 3/50273* (2013.01); *B01L 3/502715* (2013.01); *B01L 3/502761* (2013.01); *B01L 3/502753* (2013.01); *B01L 2200/0647* (2013.01); *B01L 2300/0609* (2013.01); *B01L 2300/069* (2013.01); *B01L 2300/0681* (2013.01); *B01L 2300/0822* (2013.01); *B01L 2300/0838* (2013.01); *B01L 2300/0887* (2013.01); *B01L 2400/0406* (2013.01); *B01L 2400/0409* (2013.01); *G01N 2333/90216* (2013.01); *G01N 2800/28* (2013.01); *G01N 2800/2814* (2013.01); *G01N 2800/2821* (2013.01)

(58) Field of Classification Search
None
See application file for complete search history.

(56) References Cited

U.S. PATENT DOCUMENTS 3,914,985 A 10/1975 von Behrens
7,070,739 B1 7/2006 Anderson et al.
(Continued)

FOREIGN PATENT DOCUMENTS

EP 0357272 3/1990
WO 96/07096 3/1996
(Continued)

OTHER PUBLICATIONS

European Patent Office, Search Report for EU Application No. 16178857.5 dated Nov. 30, 2016.
(Continued)

*Primary Examiner* — Rebecca L Martinez

(57) ABSTRACT

The present invention relates to methods of diagnosing samples as well as various microfluidic, microcentrifuge and microfilter devices. In one embodiment, the present invention provides a method of diagnosing neurodegenerative diseases using mitochondrial and/or platelet samples. In another embodiment, the present invention provides a microfluidic device that selectively captures and analyzes a desired amount of target biological particle.

6 Claims, 5 Drawing Sheets

(56) References Cited

U.S. PATENT DOCUMENTS

2004/0048236 A1* 3/2004 Ben-Shachar ......... C12Q 1/008
                                                    435/4
2004/0067162 A1  4/2004 Haubert et al.
2007/0253940 A1* 11/2007 Sumida .................. A61K 35/16
                                                   424/93.72

FOREIGN PATENT DOCUMENTS

| WO | 98/19169      | 5/1998 |
| WO | WO1998/019169 | 5/1998 |
| WO | 99/45139      | 9/1999 |

OTHER PUBLICATIONS

Japanese Patent Office, Notice of Final Rejection of Application No. 2011-553054 dated Apr. 10, 2014.
European Patent Office, Search Documents for Application No. 10749228.2 dated Jul. 2012 and dated Feb. 2016.
Australian IP Office, Patent Examination Report No. 1 for Application Serial No. 2015218536 dated May 24, 2016.
Australian IP Office, Patent Examination Report No. 1 for Application Serial No. 2010221418 dated May 21, 2014.
Canadian Intellectual Property Office, Examination report for Application Serial No. 2,753,886 dated Jul. 3, 2016.
Japanese Patent Office, Notice of Reasons for Rejection of Application No. 2011-553054 dated Jun. 14, 2013.
EPO Search Report / Communication Pursuant to Article 94(3) EPC for Application No. EP 16 178 857.5 dated Jan. 24, 2019.

* cited by examiner

A.

B.

A.

B.

DIAGNOSTIC DEVICES AND METHODS OF USE

CROSS-REFERENCE TO RELATED APPLICATIONS

This application claims the benefit of priority under 35 U.S.C. § 120 as a continuation of U.S. patent application Ser. No. 13/203,333 filed Aug. 25, 2011, which is the National Phase of International Application No. PCT/US2010/025964 filed Mar. 2, 2010, which designated the U.S. and that International Application was published under PCT Article 21(2) in English, which also includes a claim of priority under 35 U.S.C. § 119(e) to U.S. provisional patent application Nos. 61/156,717 filed Mar. 2, 2009, and 61/156,734 filed Mar. 2, 2009, the entirety of which is hereby incorporated by reference.

FIELD OF THE INVENTION

The invention relates to methods of performing diagnostic analyses on tissue samples as well as microfluidic and microfilter devices.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Originally developed for producing large-scale integrated circuits, microfabrication technology has also spurred research and development efforts to manipulate and analyze complex biological fluids at the nano- and microliter scale. The development of miniaturized diagnostic devices for the clinical analysis of blood and other body fluids is an important application of this emerging technology.[1-6] For example, point-of-use blood glucose monitoring systems have demonstrated the ability of miniaturized clinical chemistry technology to improve patient care and health care delivery methods.[7,8]

Many current diagnostic technologies require sample preparation prior to analysis, and microfluidic devices can be engineered with an integrated isolation process upstream of the analyte detection region. For example, glucose test strips isolate plasma from whole blood with glass fiber filters or microporous membranes.[9] Though researchers have reported many lab-on-a-chip diagnostic advances, few results relevant to the microfluidic fractionation of samples are reported.[10] For example, Brody et al.[11] suggested separating plasma from whole blood using a microfabricated filter device, and reported the filtration of a suspension of microspheres. Wilding et al.[12] demonstrated using microfilters to measure white blood cells for genetic analysis, and Duffy et al.[13] proposed centrifugation on a rotating "lab disc." Still, the current state of the art lacks a device capable of isolating for optical visualization a desired number or numerical range of biological particles from a liquid biological sample. Such a device would be of tremendous utility in the point-of-care diagnostics environment by enabling rapid, low-cost diagnoses.

One possible application for microfluidic devices is their use in conjunction with new and reliable biomarkers for diagnosis and treatment of conditions and diseases. For example, recent research has indicated that certain functional declines specific to neurological conditions such as Alzheimer's Disease can be detected in peripheral cells, including platelets. Recent results have also indicated that these same changes can also be detected in platelets from subjects who have been diagnosed with mild cognitive impairment (MCI), often a preclinical precursor to full-blown AD, marked most often by mild memory loss ("monosymptomatic progressive amnesia").

Microfilters are well suited for microfluidic sample preparation, as they are compatible with current microfabrication technologies, and filtration can be accomplished via pressurization, capillary action, or other induced flows. Further, the precise dimensional and geometric control afforded by micromachining enables the development of optimum filter designs that are not possible with traditional membrane filtration. For example, hollow fiber membranes (commonly used for plasma separation) have bulk flow channel diameters of 200 to 400 $\mu m$, while microfluidic channels are readily constructed at dimensions commensurate with blood cells (red blood cells typically measure from 6 to 7 $\mu m$ in diameter, platelets 1-2 $\mu m$). Also, microfilter devices can be fabricated with precise pore dimensions and geometry; in contrast, pore size and geometry in microporous membranes are often heterogeneous. Finally, microfilter devices fabricated with optically transparent material can enable direct visualization of target pathology or labeling of such.

SUMMARY OF THE INVENTION

Various embodiments include a microfluidic device, comprising an upper plate, comprising an injector port in fluid communication with an optical measurement chamber; engaged with a lower plate, comprising one or more filter channels, where the surface of the optical measurement chamber abutting the lower plate is in fluid communication with the one or more filter channels. In another embodiment, the upper plate comprises more than one injector port. In another embodiment, the upper plate comprises more than one optical measurement chamber. In another embodiment, the one or more filter channels are arranged in rows of parallel lines which in any two adjacent rows slope in opposite directions. In another embodiment, the one or more filter channels are less than 1.0 $\mu m$ wide. In another embodiment, the lower plate is engaged with a capillary eluent chamber that enhances filter flow through capillary force. In another embodiment, a flow channel attaches the injector port to the optical measurement chamber. In another embodiment, the lower plate is made of glass. In another embodiment, the upper plate is made of glass. In another embodiment, one or more temperature controllers adapted to regulate temperature within the optical measurement chamber. In another embodiment, the optical measurement chamber is configured to retain molecules on the basis of affinity, size, charge or mobility. In another embodiment, the optical measurement chamber is configured to retain within 5% of a target number of biological particles. In another embodiment, the optical measurement chamber is configured to retain within 2% of a target number of biological particles. In another embodiment, the optical measurement chamber is configured to retain within 1% of a target number of biological particles. In another embodiment, the device is adapted such that the flow of fluid from the injector port to the optical measurement chamber is regulated by pressure, valves, or other similar components.

Other embodiments include a microfluidic kit for the diagnosis of Alzheimer's Disease and/or mild cognitive impairment, comprising a microfluidic diagnostic device; and instructions for use.

Other embodiments include a kit for the diagnosis of a neurodegenerative disease, comprising a centrifugal diagnostic device comprising an optical microcentrifuge tube insert and/or cuvette; and instructions for use. In another embodiment, the neurodegenerative disease is Alzheimer's Disease and/or mild cognitive impairment.

Various embodiments include a method of diagnosing a neurodegenerative disease, comprising obtaining a sample from a subject; quantifying the amount or activity of a target moiety in the sample by transferring the sample to the device described in claim 1 herein, and comparing the amount or activity of the target moiety in the sample with the amount or activity of the target moiety in a standard, wherein a change in amount or activity of the target moiety relative to the standard indicates that the subject has or will develop a neurodegenerative disease. In another embodiment, the sample comprises an unprocessed sample. In another embodiment, the sample comprises a peripheral tissue sample. In another embodiment, the target moiety comprises mitochondrial protein. In another embodiment, the sample does not contain mitochondrial isolate and/or selection. In another embodiment, the sample has not been exposed to a high-energy disruption technique. In another embodiment, the sample has not been exposed to sonication, nitrogen cavitation and/or lysis procedure. In another embodiment, quantifying the amount or activity of a target moiety comprises determining the cytochrome oxidase activity in the tissue sample. In another embodiment, quantifying the amount or activity of a target moiety comprises determining the amount of amyloid precursor protein present in the unprocessed sample. In another embodiment, the sample comprises plasma. In another embodiment, the sample comprises platelet-rich plasma (PRP). In another embodiment, the subject is mammalian. In another embodiment, the subject is a human. In another embodiment, the neurodegenerative disease is at least one of Alcoholism, Alexander's disease, Alper's disease, Alzheimer's Disease, amyotrophic lateral sclerosis (ALS), Ataxia telangiectasia, Batten disease, Bovine spongiform encephalopathy (BSE), Canavan disease, Cerebral palsy, Cockayne syndrome, Corticobasal degeneration, Creutzfeldt-Jakob disease, Frontotemporal lobar degeneration, huntington's disease, HIV-associated dementia, Kennedy's disease, Krabbe's disease, Lewy body dementia, Neuroborreliosis, Machado-Joseph disease, Multiple System Atrophy, Multiple sclerosis, Narcolepsy, Niemann Pick disease, PD, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease, Spinocerebellar ataxia, Spinal muscular atrophy, Steele-Richardson-Olszewski disease, and Tabes dorsalis. In another embodiment, the targeting moiety comprises mitochondrial translocase subunit. In another embodiment, the targeting moiety comprises amyloid precursor protein, or fragments thereof, complexed with mitochondrial protein.

Other embodiments include a method of diagnosing a neurodegenerative disease, comprising obtaining a sample from a subject; quantifying the amount or activity of a target moiety in the sample by transferring the sample to a centrifugal device; and comparing the amount or activity of the target moiety in the sample with the amount or activity of the target moiety in a standard, wherein a change in amount or activity of the target moiety relative to the standard indicates that the subject has or will develop a neurodegenerative disease. In another embodiment, the centrifugal device comprises an optical microcentrifuge tube insert and/or cuvette.

Other features and advantages of the invention will become apparent from the following detailed description, taken in conjunction with the accompanying drawings, which illustrate, by way of example, various embodiments of the invention.

BRIEF DESCRIPTION OF THE DRAWINGS

Exemplary embodiments are illustrated in referenced figures. It is intended that the embodiments and figures disclosed herein are to be considered illustrative rather than restrictive.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As used herein, the term "diagnose" or "diagnosis" refers to determining the nature or the identity of a condition or disease. A diagnosis may be accompanied by a determination as to the severity of the disease.

As used herein, "prognostic" or "prognosis" refers to predicting the outcome of a disease.

As used herein, "AD" means Alzheimer's Disease.

As used herein, "MCI" means mild cognitive impairment.

As used herein, the term "PD" means Parkinson's Disease.

As used herein, "fluid connection" means a connection comprising a liquid connector, such as, for example, water, blood, plasma, and the like.

As used herein, an "unprocessed sample" refers to a sample that has not been exposed to high-energy disruption techniques such as sonication or nitrogen cavitation. As an example, although the term is in no way so limited, an unprocessed sample containing platelet rich plasma may not be exposed to the filtration, purification and/or isolation of the mitochondria itself before being analyzed for mitochondrial enzyme dysfunction.

As used herein, the term "herringbone" pattern refers to a pattern made up of rows of parallel lines which in any two adjacent rows slope in opposite directions.

As used herein, upper and lower plates of a microfluidic device may also refer to different sides or areas of a single attached device. For example, although in way limiting, a microfluidic device with an upper and lower plate may refer to a single attached device with one side containing an injector port and the opposite side containing various channels.

As used herein, "microfluidics" refers to a device that allows for flow of fluid, suspensions or suspended particles at various dimensions and scales of size.

Microfluidics and Flow Devices

Figure 1:
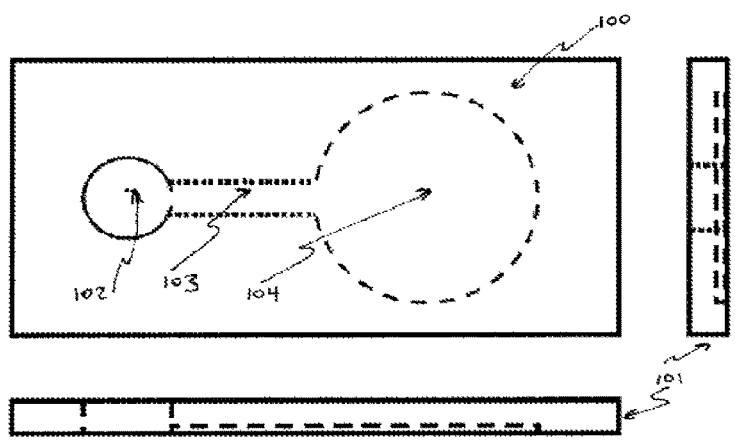
FIG. 1 depicts, in accordance with an embodiment herein, a schematic of a microfluidics device that will allow densitometric measurement of the stained suspended-cell sample. The general design may be microfabrication technology, containing sandwich design where surface etched features become internal features when assembled. This device may contain two etched glass plates that, when assembled and bonded, form an internal network of interconnected channels and chambers. (A) discloses the upper plate in both a top view 100 and side views 101. The upper plate contains an injector port 102 for injection of the sample suspended in buffer, a flow channel 103 leading to a optical measurement chamber 104 that lies over filter channels 107 etched into the lower plate. (B) discloses the lower plate in both a top view 105 and side views 106. In one embodiment, six to eight of these devices may be arrayed on a chip designed to the format of 96-well plates, to be read in a standard microplate reader.
Figure 1:
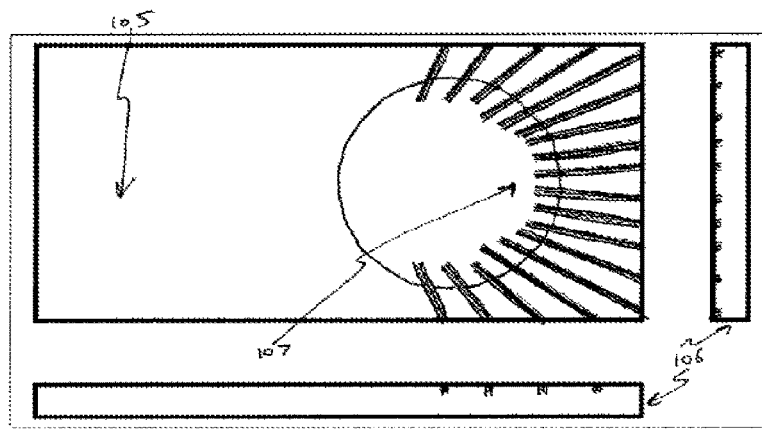
Figure 2:
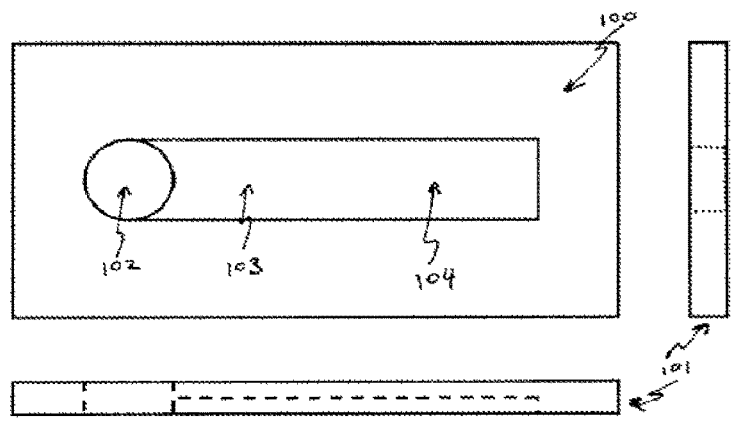
FIG. 2 depicts, in accordance with an embodiment herein, a schematic of a microfluidics device that will allow densitometric measurement of stained suspended-cell sample. The general design may be microfabrication technology, containing sandwich design where surface etched features become internal features when assembled. (A) discloses the upper plate in both a top view 100 and side views 101. The upper plate contains an injector port 102, drilled through, (e.g., for 21G=0.8 mm outer diameter needle). The upper plate also contains a flow channel 103, 1 mm wide×500 µm high, leading to an optical measurement chamber 104 overlaying filter channels 107 in traverse flow, with length variable. (B) discloses the lower filter plate in both a top view 105 and side views 106, with the lower filter plate dimensionally smaller than the upper plate. The filter channels 107 in the lower filter plate are in a herringbone pattern of shallow transverse flow filter channels, less than 1.0 µm wide, with depth indeterminate. In one embodiment, there may also be a lower capping plate, featureless and dimensionally identical to the upper plate, including a capillary eluent chamber 108 formed by the lower capping plate or wicking absorbent.
Figure 2:
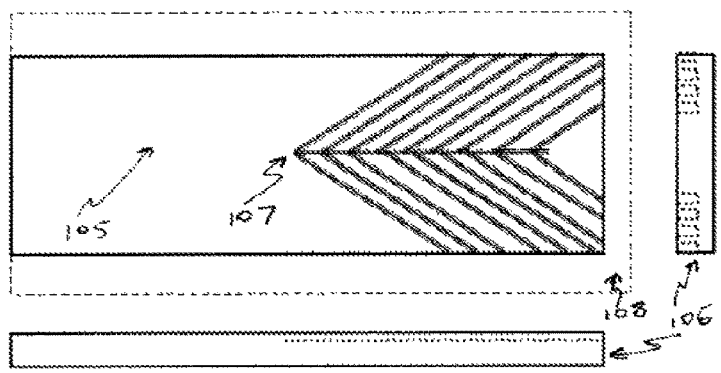

As disclosed herein, in accordance with various embodiments herein, the inventors created microfluidic devices with filter channels 107 placed so as to be fluidly connected to an optical measurement chamber 104 when the components are joined together. The filter channels 107 can allow liquid to flow from the optical measurement chamber 104 while blocking the flow of, for example, suspended blood cells. In another embodiment, the microfluidic device is described in FIGS. 1, 2, 3 and/or 4 herein.

Embodiments of the invention include a microfluidic diagnostic device. In certain embodiments, the device can isolate biological particles from liquid samples. In certain embodiments the particles can be, for example, erythrocytes, leukocytes, platelets, fibroblasts, cultured cells, and the like. Likewise, in certain embodiments, the liquid sample can be whole blood, whole blood fractions, plasma, urine, lymph, broth, media, or the like.

Embodiments of the invention can be fabricated from any suitable material, such as, for example, plastic, glass, silica, composites, or the like.

In embodiments that include plastic materials, the plastic materials can include, for example, thermoplastics, such as, for example, acrylonitrile butadiene styrene plastics (ABS), acetals, acrylic (Perspex), acrylo-nitrile (nylon), cellulosics, fluoroplastics, high-density polyethylene (HDPE), low-density polyethylene (LDPE), Noryl, polyarylates, polyarylsulfones, polybutylenes, polybutylene terephthalate (PBT), polycarbonates, polyesters, polyetherimides, polyetherketones, polyethylene (polythene), polypropylene, polyallomers, polyethylene terephalate, polyimides, polyamide-imides, poly vinyl acetate (PVA), poly vinyl chloride (PVC), polystyrene, polysulfones, Styrene, ABS PTFE (Teflon), and the like.

In embodiments that include plastic materials, the plastic materials can be, for example, thermosets, such as, for example, alkyd polyesters, allyls, bakelite, epoxy, melamine, phenolics, polybutadienes, polyester, polyurethane, silicones, ureas, and the like. Likewise, the plastic materials can include bioplastics. Bioplastics are a form of plastics derived from renewable biomass sources, such as vegetable oil, corn starch, pea starch, or microbiota, rather than traditional plastics that are often derived from petroleum. Types of bioplastics suitable for use with embodiments of the invention include, for example, polylactide acid (PLA) plastics, poly-3-hydroxybutyrate (PHB), polyamide 11 (PA 11), bio-derived polyethylene, and the like.

In certain embodiments, the device can be composed of, for example, a single component. In certain embodiments, the device can be composed of multiple components, such as, for example, an upper plate and lower plate. In some embodiments, the multiple components can be made from the same or different materials. In certain embodiments, the components can be homogenous or heterogenous, and can include, for example, channels, ducts, chambers, voids, ports, and the like. In heterogenous embodiments the channels, ducts, chambers, voids, ports, and the like, can be of consistent size, such as, for example, 1 μm in depth or diameter, or 2 μm in depth or diameter, or 4 μm in depth or diameter, or 10 μm in depth or diameter, or more, or the like. Likewise, in heterogenous embodiments the channels, ducts, chambers, voids, ports, and the like, can range in size, such as, for example, between 1 and 3 μm in depth or diameter, between 3 and 6 μm in depth or diameter, between 6 and 10 μm in depth or diameter, or more, or between 1 and 2 mm in depth or diameter, or between 2 and 5 mm in depth or diameter, or between 5 and 10 mm in depth or diameter, or more, or the like.

In some embodiments composed of multiple components, the multiple components can be sealed to form a single unit. In certain embodiments, a chamber of the device can capture a predetermined number, amount, or volume of the target biological particle. Likewise, certain embodiments of the device can maintain the capture of a predetermined number or amount of the target biological particle. Likewise, in certain embodiments a chamber of the device can capture within 0.1%, 0.5%, 1%, 2%, 4%, 7%, 10%, 15%, or 20% or any other desirable amount of a predetermined number or amount of particles.

In certain embodiments, the predetermined number or amount can be within, for example, a range, such as from 0 to 100 particles, or from 100 to 1000 particles, or from 1000 to 10,000 particles, or from 10,000 to 100,000 particles, or from 100,000 to 1,000,000 particles, or from 1,000,000 to 5,000,000 particles, or within any of these ranges, or more, or the like.

In some embodiments the optical measurement chamber 104 can be optically transparent, such that the biological particles within the chamber can be visualized. In certain embodiments the visualization can be achieved via any suitable means, such as, for example, densitometric/spectrophotometric readers, luminescent/fluorometric readers, or the like. In certain embodiments, the size and configuration of the measuring chamber can be optimized for a particular target biological particle.

Embodiments of the invention can include at least one filter channel 107 arranged to drain liquid from the optical measurement chamber 104.

In an embodiment, the present invention provides a device comprising:

(a) an upper plate, including an injector port 102 in fluid connection with an optical measurement chamber 104; and;

(b) a lower plate, including at least one filter channel 107;

(c) wherein the surface of the optical measurement chamber 104 abutting the lower plate is in fluid connection with the at least one filter channel 107.

In an embodiment, the present invention provides a method of diagnosing, for example, the presence, absence, or severity of a disease. Likewise, in some embodiments the invention provides a method of diagnosing the likelihood of developing or not developing a disease. In certain embodiments, the disease can be, for example, AD, PD, other neurodegenerative diseases, or the like. In certain embodiments, the method can include providing a biological sample, manipulating the sample so as to be able to visualize certain characteristics of the sample, loading the sample into a device of the present invention, and visualizing the sample.

Advantages of the design include utilization of easily-attainable, low-volume blood sample that can be processed and measured in <2 hours. Also, the novel microfluidics measurement device enables rapid densitometric (or fluorescent or luminescent) measurement of labeled sample. The reaction product in device is measurable in a microplate reader after simple reaction steps—designed for possible use in basic clinical labs, with basic equipment, by minimally trained lab personnel. Various embodiments may measure a cellular function that has been repeatedly found deficient in Alzheimer's Disease brain, for example, platelets and other tissues, and measure it with increased sensitivity in whole, unlysed cells—in other words, unprocessed samples, not relying on mitochondrial isolation, which is the largest confound in conventional ETC enzyme studies. The device, in particular, has broad application in other diseases, as it is usable for a broad range of dyes, reactions, and probes, including antibody-based techniques, and can be modified for different cell types (e.g., lymphocytes, cultured lines) in clinical and research applications.

Diagnostic Methods Using Mitochondria

As disclosed herein, recent research has indicated that the mitochondrial electron transport chain (ETC) enzymes are functionally deficient in AD as well as mild cognitive impairment (MCI). These specific deficiencies (particularly in the enzyme cytochrome oxidase) have been found in brain and in platelets from AD patients, as well as in other peripheral tissues (that are somewhat less accessible; e.g., muscle). The inventors have found a significant decrease in the function of cytochrome oxidase (C.O.) in platelet mitochondria isolated from subjects with MCI, supporting the view that interference with mitochondrial function is an early and detectable systemic event in AD pathophysiology which can be leveraged as a biomarker of the disease.

In an embodiment, the present invention provides a method of diagnosing a neurodegenerative disease, comprising:

(a) providing a tissue sample from a subject;

(b) quantifying the amount or activity of a target moiety in the cells of said sample; and (c) comparing the amount or activity of the target moiety in the cells of the sample with the amount or activity of the target moiety in a standard, wherein a change in the amount or activity of the target moiety in the cells of the sample relative to the standard indicates that the subject has a neurodegenerative disease.

In certain embodiments, the neurodegenerative disease can be, for example, Alcoholism, Alexander's disease, Alper's disease, AD, ALS, Ataxia telangiectasia, Batten disease (also known as Spielmeyer-Vogt-Sjogren-Batten disease), Bovine spongiform encephalopathy (BSE), Canavan disease, Cerebral palsy, Cockayne syndrome, Corticobasal degeneration, Creutzfeldt-Jakob disease, Frontotemporal lobar degeneration, HD, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, PD, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis.

In some embodiments, the tissue sample can comprise, for example, amniotic fluid, blood, cerebro-spinal fluid, plasma, serum, synovial fluid, other biofluids, or the like. Certain embodiments can utilize fractionated samples, such as, for example, blood fractions, plasma fractions, or the like. Some embodiments can utilize platelet-rich plasma (PRP). In embodiments utilizing fractionated samples, the fractionation can be accomplished using, for example, differential centrifugation, or the like. In certain embodiments, the tissue sample can be obtained from the subject via, for example, amniocentesis, a blood draw, a spinal tap, or the like.

In some embodiments, the tissue sample can comprise, for example, muscle cells, muscle fibers, or muscle tissue, such as cardiac muscle tissue, smooth muscle tissue, or skeletal muscle tissue, or the like. In certain embodiments, the tissue sample can be obtained via, for example, a biopsy, or the like.

In certain embodiments, the subject can be a mammal, such as, for example, a marsupial, a monotreme, a placental mammal, or the like. In embodiments utilizing a placental mammal, the placental mammal can be, for example, a human, or the like. In some embodiments, quantifying the amount or activity of a target moiety can be accomplished via, for example, histochemical techniques, immunochemical techniques, a combination thereof, or the like.

In certain embodiments, quantifying the amount or activity of a target moiety can mean, for example, quantifying the presence of a protein, such as, for example, amyloid beta (Aβ), amyloid precursor protein (APP), mitochondrial translocase (subunit TOMM40), the APP-TOMM40 complex, or the like. In some embodiments, quantification can be achieved with the use of antibodies reactive to the target moiety.

In certain embodiments, quantifying the amount or activity of a target moiety can mean, for example, assessing enzyme activity. In some embodiments, this can involve, for example, densitometric/spectrophotometric assessment, fluorometric assessment, histochemical labeling, or the like.

In certain embodiments, the standard amount or activity of a target moiety can be determined from, for example, patient samples, literature, computer databases, or a combination thereof, or the like. In some embodiments, the change in amount or activity of a target moiety can be, for example, an increase or a decrease.

In certain embodiments, the cells in which the amount or activity of a target moiety is to be tested can be, for example, any mitochondria-containing cell, such as thrombocytes, or the like.

Certain embodiments of the invention utilize diagnostic test formats such as, for example, cuvettes, multi-well plates, microfilter devices, or the like. In some embodiments the multi-well plates can include, for example, 4 wells, 6 wells, 12 wells, 24 wells, 48 wells, 96 wells, 192 wells, 384 wells, 768 wells, 1536 wells, or more, or the like. In some embodiments the microfilter device can include, for example, a fill port, an optically transparent measurement chamber, and at least one drainage channel. In some embodiments the microfilter device can be fabricated from plastic, glass, silica, or the like.

Kits

Embodiments of the invention are also directed to a kit, both for diagnosing the presence of, absence of, severity of, or likelihood of developing or not developing a neurodegenerative disease, as well as preparation and use of a microfluidic and centrifugal device. The kit is an assemblage of materials or components, suitable for performing a method of the invention. Thus, in some embodiments the kit describes a method of the invention, as described above or in the following examples.

The exact nature of the components configured in the inventive kit depends on its intended purpose. For example, some embodiments are configured for the purpose of diagnosing neurodegenerative diseases. In one embodiment, the kit is configured particularly for the purpose of diagnosing AD. In another embodiment, the kit is configured particularly for the purpose of diagnosing PD. Or, in some embodiments, the kit contains a device including upper plate and lower plate with an injector port 102 in fluid communication with an optical measurement chamber 104, as described above.

Instructions for use may be included in the kit. "Instructions for use" typically include a tangible expression describing the technique to be employed in using the components of the kit to effect a desired outcome, such as to diagnose the presence of AD in a human. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive devices and the like. The packaging material is constructed by well known methods, preferably to provide a sterile, contaminant-free environment. The packaging materials employed in the kit are those customarily utilized in diagnostic assays. As used herein, the term "package" refers to a suitable solid matrix or material such as glass, plastic, paper, foil, and the like, capable of holding the individual kit components. Thus, for example, a package can be a plastic container used to contain suitable quantities of an inventive device. The packaging material generally has an external label which indicates the contents and/or purpose of the kit and/or its components.

Diagnostic Protocols

As disclosed herein, various embodiments include a method of diagnosing a disease and/or condition in a subject by one or more of combinations of the following steps: (1) obtaining a sample from a subject 200; (2) staining of the sample 201; (3) transfer to a microfluidic device 202, where (4) the carrier solution may pass through while stained sample are retained 203, and then (5) diagnosing the subject by measuring the optical density and comparing the density to a standard 204.

In one embodiment, the staining of the sample 201 includes drawing blood from a subject into a centrifuge tube containing anti-coagulant. In another embodiment, the blood is centrifuged, followed by aspirating the PRP (platelet-rich plasma) layer, acidifying the PRP by initially adding ACD, then adding the ACD dropwise while checking the pH of the PRP. In another embodiment the PRP is diluted with Phosphate Buffered Saline (PBS), centrifuged, and then supernatant transferred. In another embodiment, the supernatant is centrifuged to pellet the platelets and then resuspended in Modified Tyrode's Buffer. In another embodiment, the platelets in Modified Tyrode's Buffer are added to tubes with an equivalent volume of 2× reaction staining solution. In another embodiment, the tubes are incubated, centrifuged, resulting pellets resuspended, and then transferred to a microfluidic and/or centrifuge device for quantification.

In one embodiment, the transfer of stained samples to the injector port 102 of the microfluidic device for quantification may be by manual injection such as via syringe. In another embodiment, the transfer may be in an automated fashion, as by infusion pump or other device. In another embodiment, the stained platelet suspension will flow, under pressure of application (e.g., syringe or pump) through an internal channel(s) to the optical measurement chamber 104, which overlies the filtration channels 107. As described herein, the filtration channels 107 may be aligned to maximize platelet carrier solution (i.e., buffer) pass-through while retaining the platelets in the optical measurement chamber 104. In another embodiment, the filtration channels 107 are designed to enhance carrier solution pass-through via capillary forces and thereby enhance platelet packing density in the optical measurement chamber 104. Thus, in another embodiment, the carrier solution drainage and concomitant platelet packing may be achieved via two forces: the force of application and capillary force in the drainage channels. As the carrier solution is pulled from the optical measurement chamber 104, platelet packing density reaches a maximal, and thus constant, value, suitable for the control of subsequent measurements of staining density within the platelets.

In another embodiment, the optical density of the optical measurement chamber 104 may be measured at an established wavelength and the result compared against a tabled value. In another embodiment, the optical density of the optical measurement chamber 104 may be measured in concert with an included standard reference material. This measurement can be achieved, for example, by housing the microfluidics apparatus, or multiple apparatus for greater economy, in a manufactured plate or frame with the dimensions of a standard microplate (e.g., 96-well microplate), with the optical measurement chamber 104 aligned with standard coordinates of a multiwell microplate. Thus, in another embodiment, one may use a standard microplate reader to select the specified well coordinates and specified wavelength as they are accustomed, and perform measurement. Another embodiment may incorporate the microfluidics apparatus on the vertical and housed in a frame with the dimensions of a standard spectrophotometer cuvette, such that the optical measurement chamber 104 aligned with the standard beam of a spectrophotometer. In designs targeting measurement in a spectrophotometer or spectrophotometric microplate reader, spectrophotometric measurement at designated wavelengths is used as a proxy for densitometric measurement. Thus, in another embodiment, alternate wavelengths could be designated, and may or may not incorporate various correction factors, for use in non-monochromator-equipped spectrophotometric devices or when the designated wavelength cannot be otherwise used. Another embodiment may incorporate similar microfluidics design characteristics but enabling direct measurement in an optical densitometer. Each described embodiment would be equally valid and each could be provided as a kit targeted to the user's available device (e.g., "diagnostic kit for microplate readers", "diagnostic kit for spectrophotometers").

As further disclosed herein, various embodiments include a method of diagnosing a disease and/or condition in a subject by one or more of combinations of the following steps: (1) a sample may be obtained from the subject 200; (2) followed by staining of the sample 201; and (3) transfer of the stained sample to a centrifugal device 205; (4) centrifuged to induce sedimentation of stained sample 206; and then (5) measuring the optical density and comparing the density to a standard 207.

Figure 3:
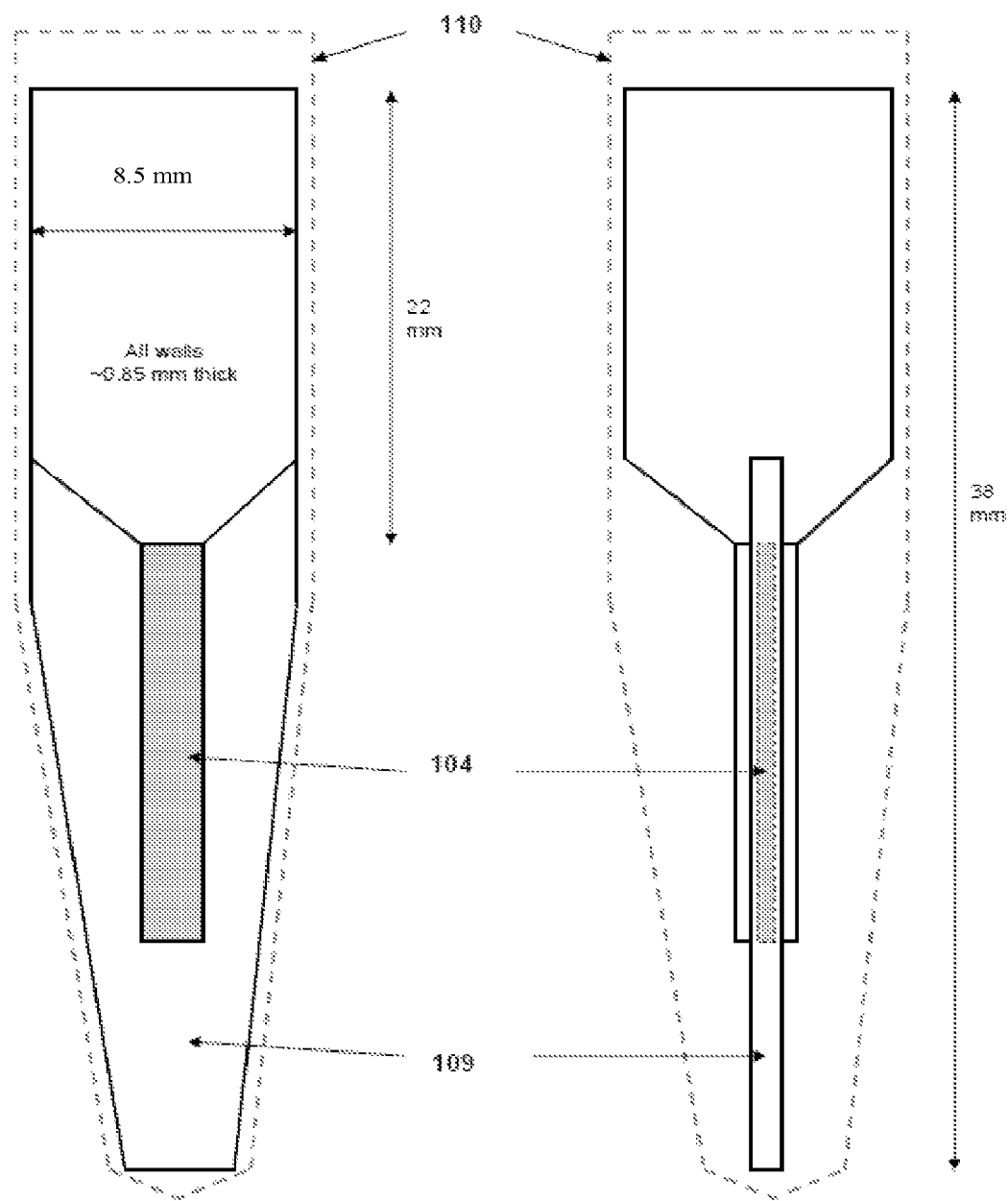
FIG. 3 depicts, in accordance with an embodiment herein, an insert design to allow densitometric measurement of stained suspended cell sample using microcentrifuge. The insert may act similar to a microcentrifuge tube insert where the stained particles, such as platelets, may reliably pellet into the optical pocket of the insert for standardized optical measurement. The figure depicts a tube 110 with typical dimensions of a 1.5 mL tube, an optical measurement chamber 104 for the insert, which may have, for example, inner dimensions of 2 mm width by 14 mm, 0.5-1.0 mm diameter. The figure also depicts a support fin 109 which may be, for example, about 0.85 mm thick. In one embodiment described in further detail herein, the staining intensity of the platelets will decrease in Alzheimer's Disease patients, and in pre-symptomatic subjects, and one will be able to reliably measure this decrease.

In another embodiment, the transfer of the stained sample to a centrifugal device may include transfer to a tube insert as described in FIG. 3 herein. In another embodiment, the tube insert is placed within a standard 1.5 ml microcentrifuge tube 110, the stained platelet suspension is transferred (e.g., via pipette) into the tube insert, and the tube and insert are centrifuged at a determined speed (e.g., 2000×g) for a determined time (e.g., 15 min) to induce the sedimentation of the stained platelets into the optical measurement chamber 104, or "optical pocket". Thus, under constant centrifugal force, stained platelet packing density within the measurement chamber reaches a maximal, and thus constant, value, suitable for the control of subsequent measurements of staining density within the platelets.

In another embodiment, the optical density of the optical measurement chamber is measured at an established wavelength (e.g., 330 nm) and the result compared against a tabled value, or in concert with an included standard reference material. In another embodiment, this measurement can be achieved, for example, by providing a manufactured plate or frame with the dimensions of a standard microplate (e.g., 96-well microplate), with the measurement chamber aligned with standard coordinates of a multiwell microplate by way of providing for the insertion of the tube insert into the frame. Thus, in any standard microplate reader, the user may select the specified well coordinates and specified wavelength as they are accustomed, and perform measurement. Another embodiment may incorporate a frame with the dimensions of a standard spectrophotometer cuvette 111, such that the optical measurement chamber 104 is aligned with the standard beam of a spectrophotometer upon insertion. In designs targeting measurement in a spectrophotometer or spectrophotometric microplate reader, spectrophotometric measurement at designated wavelengths is used as a proxy for densitometric measurement. Thus, in another embodiment, alternate wavelengths could be designated, and may or may not incorporate various correction factors, for use in non-monochromator-equipped spectrophotometric devices or when the designated wavelength cannot be otherwise used. Another embodiment may incorporate similar microfluidics design characteristics but enabling direct measurement in an optical densitometer. Each described embodiment would be equally valid and each could be provided as a kit targeted to the user's available device (e.g., "diagnostic kit for microplate readers", "diagnostic kit for spectrophotometers").

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Kit Design to Provide Simple and Low Cost Histochemical Assessment

Recent research has demonstrated that certain neurological declines (such as in Alzheimer's Disease), can be detected in peripheral cells, such as platelets. By histochemically staining the activity of an enzyme of interest without activating the platelets (i.e., keep whole platelets in suspension throughout the procedure), the platelets can be forced into a tissue-like orientation for densitometric measurement of reaction product using a microfluidic device, without relying on the complicated methodology needed for activation and adherence. This in turn removes the need for a secondary control assay, and there is a reduction in the number of separate reagents and other supplies necessary, further reducing the overall cost and complication of the assay. For instance, the inventors can achieve a pure platelet preparation using differential centrifugation in generic low-cost tubes (e.g., evacuated ACD tubes; tested and confirmed by staining for contamination), rather than requiring a commercial separation tube with separation media (e.g., Sigma-Aldrich Accuspin, Vacutainer CPT). The inventors have tested and eliminated common anti-platelet activation factors prostaglandin-1 and apyrase, relying only on acid-citrate-dextrose anticoagulant.

The inventors have designed a microfluidics device that captures/filters stained platelets, in a uniform array within an optical measurement chamber, while allowing flow-through of the carrier buffer, measuring the staining product with highest sensitivity. The device provides unprecedented sensitivity in the measurement of the staining product, and thus, unprecedented sensitivity and accuracy in the measurement of the enzyme activity itself. This device can also be used as a high-quality cell filter, with or without simple modifications, for optical measurement of any number of modalities (e.g., fluorescence, luminescence) across many types of suspension cells (e.g., lymphocytes, cancer cells). Thus, the number of potential applications for a device of this type, both in the clinic and in the laboratory, is nearly endless.

Example 2

Microfluidics Plate Design

The general microfluidics plate design allows densitometric measurement of the stained suspended-cell sample. The general design incorporates microfabrication technology, including a sandwich design where surface etched features become internal features when assembled. The device may have, for example, two etched glass plates that, when assembled and bonded, form an internal network of interconnected channels and chambers. The upper plate may contain an inlet port for injection of the sample suspended in buffer, as well as a flow-through channel leading to a measurement chamber. The measurement chamber, or optical measurement chamber, lies over microfiltration channels etched into the lower plate. Six to eight of these devices may, for example, be arrayed on a chip designed to the format of 96-well plates, to be read in a standard microplate reader.

Example 3

Design Characteristics of the Microfluidics Plate Design

With the design primarily a simple flow-through application, the critical test parameters are flow and filtration, i.e., the lack of 'clogging' and the ability to create a uniform measurement field. In testing of the platelet histochemistry, maintenance of anti-coagulant successfully prevented the aggregation and activation of platelets throughout the histochemical procedure. An additional parameter is the filtration of carrier buffer from the measurement chamber, such that the platelets form a homogenous layer amenable to densitometric measurement. This is key to one of the simplest variant of this design: to obtain a uniform array of platelets within the measurement chamber, the user may forgo the use of a secondary control assay, relying only on "platelet density" as an internal control.

a. The inlet port may be of the type commonly used in microfabrication design.

b. The flow channel. The flow channel will allow the unhindered flow of suspension to the measurement chamber. Modifications to the flow channel could be utilized, for example, such as the incorporation of microfabricated pressure control valves that may prove useful in establishing the consistency of platelet packing density.

c. The measurement chamber. In one embodiment, the dimensions of the measurement chamber require the device's fabrication from a material of high stiffness (e.g., glass rather than commonly microfabricated plastics) for two main reasons: 1) reliable platelet packing density cannot be achieved in a flexible chamber, 2) the proposed dimensions (diameter:height/depth) could lead to collapse of the chamber with softer materials. In one embodiment, the diameter of the chamber could be a maximum of 3 mm. Measurement of the reaction product in the visual spectrum requires optical clarity above and below the sample, thus glass may be used. An important principal in absorption or densitometric assessment is the scatter of light from an irregular surface (i.e., the tissue); in tissue staining applications described herein, this is minimized by the use of glass slides and coverslips, and the macro-scale assessments typically performed (e.g., brain regional analysis) are relatively insensitive to any residual scatter. With a desire to measure the optical density of the staining product in standard, yet more sensitive, lab equipment such as a microplate reader, rather than a novel assembly of light source, optics, and detector that would have to be purchased by the enduser, light scatter by an irregular sample surface becomes much more significant. In one embodiment, this may be addressed in one of two ways: 1) minimizing the thickness of the tissue through which the beam must pass (the depth of the chamber), and 2) utilizing the glass surfaces of our device to force the sample into near-perfect perpendicular and regular alignment to the beam.

d. Microfiltration. Microfiltration channel devices are designed to passively filter plasma from whole blood, for downstream chemistry, using only capillary action. The design allows reliable filter of platelets in suspension, capturing them in the measurement chamber, uniformly without clogging, at any given unit of application. Also, rather than rely only on the front-end application pressure (injection force) to drive cell packing, one could also leverage capillary forces on the back-end, to "pull" the platelet suspension into the chamber and maximize packing uniformity. Thus, rather than simply existing as a simple slotted drain or filter, the filtration channels on the lower plate can take on an active role in preventing clogging and increasing cell density uniformity.

Example 4

Studies Demonstrating Applicability of Technique

First, assessments were made of maintenance of platelets in suspension. The degree of anti-coagulation necessary to maintain platelets without activation and binding has been assessed, and the redundant application of platelet inhibitory factors such as apyrase and prostaglandin (PGE1) has been dropped. This further reduces both the complexity and the cost of this assay. Secondly, non-cytochrome c oxidase-mediated DAB reactivity was assessed. Peroxidase activity is the largest contributor to background DAB reactivity in most DAB labeling applications, but the inventors' testing utilizing potassium cyanide inhibition of cytochrome c oxidase to reveal other reaction mechanisms has indicated that its activity is relatively low (and is lowered by increasing platelet washes).

Example 5

Measurement of Cytochrome C Oxidase Activity—Unprocessed Sample Staining 10 mL whole is blood drawn from a test subject into a centrifuge tube or tubes, containing anti-coagulant. The blood is centrifuged at 300 RCF for 15', then the PRP (platelet-rich plasma) layer is aspirated to 15 mL tube(s).

| Preparation of ACD Anticoagulant | |
|---|---|
| Step No. | Action |
| 1 | Dissolve 1.32 g of sodium citrate in 85 ml of distilled water. |
| 2 | Dissolve 0.48 g of citric acid in the solution from step 1. |
| 3 | Dissolve 1.47 g of dextrose in the solution from step 2. |
| 4 | Add distilled water to 100 ml. |
| 5 | Filter sterilize through 0.2 um filter. |

The PRP is acidified to pH 6.5 by initially adding 300 μL of ACD, then adding the ACD dropwise while checking the pH of the PRP. Next, the PRP is diluted to 5 mL with Phosphate Buffered Saline (PBS). The PRP is then centrifuged at 600 RCF for 10' at room temperature. The supernatant is then transferred to a new 15 mL tube, and the pellet is discarded.

The supernatant is centrifuged at 2000 RCF for 10' to pellet the platelets, which are then resuspended in 300 μL/8 ml blood draw of Modified Tyrode's Buffer prepared as follows:

| Preparation of Modified Tyrode's Buffer | |
|---|---|
| Step No. | Action |
| 1 | Dissolve 0.8 g of NaCl in 85 ml of distilled water. |
| 2 | Dissolve 0.02 g of KCl in the solution from step 1. |

| Preparation of Modified Tyrode's Buffer | |
|---|---|
| Step No. | Action |
| 3 | Dissolve 0.02 g of $CaCl_2$ in the solution from step 2. |
| 4 | Dissolve 0.01 g of $MgCl_2 \cdot 6H_2O$ in the solution from step 3. |
| 5 | Dissolve 0.005 g of $NaH_2 PO_4$ in the solution from step 4. |
| 6 | Dissolve 0.1 g of $NaHCO_3$ in the solution from step 5. |
| 7 | Dissolve 0.1 g of glucose in the solution from step 6. |
| 8 | Add distilled water to 100 ml. |
| 9 | Filter sterilize through 0.2 um filter. |

The staining solutions (at 2×) are prepared as follows:

| Preparation of 2X Staining solutions | |
|---|---|
| Step No. | Action |
| 1 | Measure 8 mL of 20 mM PBS. |
| 2 | Dissolve 0.0012 g of cytochrome c in the liquid from step 1. |
| 3 | Add 40 μL dimethyl sulfoxide (DMSO) to the solution from step 2; mix well. This solution will be used for the control reactions. |
| 4 | To 4 mL of the solution from step 3 is added 0.004 g diaminobenzidine (DAB); mix well. |

The reaction staining solution is then heated to 37 C.
Platelets in Tyrode's are added to tubes with an equivalent volume of 2× reaction staining solution. The tubes are closed and incubated for 1 hour in a 37 C water bath. The tubes are then centrifuged at 1600 RCF for 10' at room temperature.

The resulting pellets are resuspended, and may then be transferred to either microfluidic or centrifugal device for quantification.

Example 6

Measurement of Cytochrome C Oxidase Activity—Transfer to Microfluidic Device

After following the protocol as outlined in Example 5 above, the resulting pellets are resuspended and transferred to the microfluidic device described herein. The application of stained platelets can be, for example, by manual injection via syringe, or in an automated fashion, as by infusion pump or other device. The stained platelet suspension will flow, under pressure of application (e.g., syringe or pump) through the internal channel(s) to the measurement chamber, which overlies the microfiltration channels. The microfiltration channels are aligned to maximize platelet carrier solution (i.e., buffer) pass-through while retaining the platelets in the measurement chamber. The microfiltration channels are designed to enhance carrier solution pass-through via capillary forces and thereby enhance platelet packing density in the measurement chamber. Thus, the carrier solution drainage and concomitant platelet packing is achieved via two forces: the force of application and capillary force in the drainage channels. Thus, as the carrier solution is pulled from the measurement chamber, platelet packing density reaches a maximal, and thus constant, value, suitable for the control of subsequent measurements of staining density within the platelets.

Next, the optical density of the optical measurement chamber is measured at an established wavelength (e.g., 330 nm) and the result compared against a tabled value, or in concert with an included standard reference material. This measurement can be achieved, for example, by housing the microfluidics apparatus, or multiple apparatus for greater economy, in a manufactured plate or frame with the dimensions of a standard microplate (e.g., 96-well microplate), with the measurement chamber aligned with standard coordinates of a multiwell microplate. Thus, in any standard microplate reader, the user may select the specified well coordinates and specified wavelength as they are accustomed, and perform measurement. Another embodiment may incorporate the microfluidics apparatus on the vertical and housed in a frame with the dimensions of a standard spectrophotometer cuvette, such that the measurement chamber aligned with the standard beam of a spectrophotometer. In designs targeting measurement in a spectrophotometer or spectrophotometric microplate reader, spectrophotometric measurement at designated wavelengths is used as a proxy for densitometric measurement. Alternate wavelengths could be designated, and may or may not incorporate various correction factors, for use in non-monochromator-equipped spectrophotometric devices or when the designated wavelength cannot be otherwise used. Another embodiment may incorporate similar microfluidics design characteristics but enabling direct measurement in an optical densitometer. Each described embodiment would be equally valid and each could be provided as a kit targeted to the user's available device (e.g., "diagnostic kit for microplate readers", "diagnostic kit for spectrophotometers").

Example 7

Measurement of Cytochrome C Oxidase Activity—Transfer to Centrifugal Device

After following the protocol as outlined in Example 5 above, the resuspended pellets are transferred to the microcentrifuge tube insert described herein. The tube insert is placed within a standard 1.5 ml microcentrifuge tube. The stained platelet suspension is transferred (e.g., via pipette) into the insert and the tube is capped. The tube and insert are then centrifuged at the determined speed (e.g., 2000×g) for the determined time (e.g., 15 min) to induce the sedimentation of the stained platelets into the measurement chamber, or "optical pocket". Thus, under constant centrifugal force, stained platelet packing density within the measurement chamber reaches a maximal, and thus constant, value, suitable for the control of subsequent measurements of staining density within the platelets.

Figure 4:
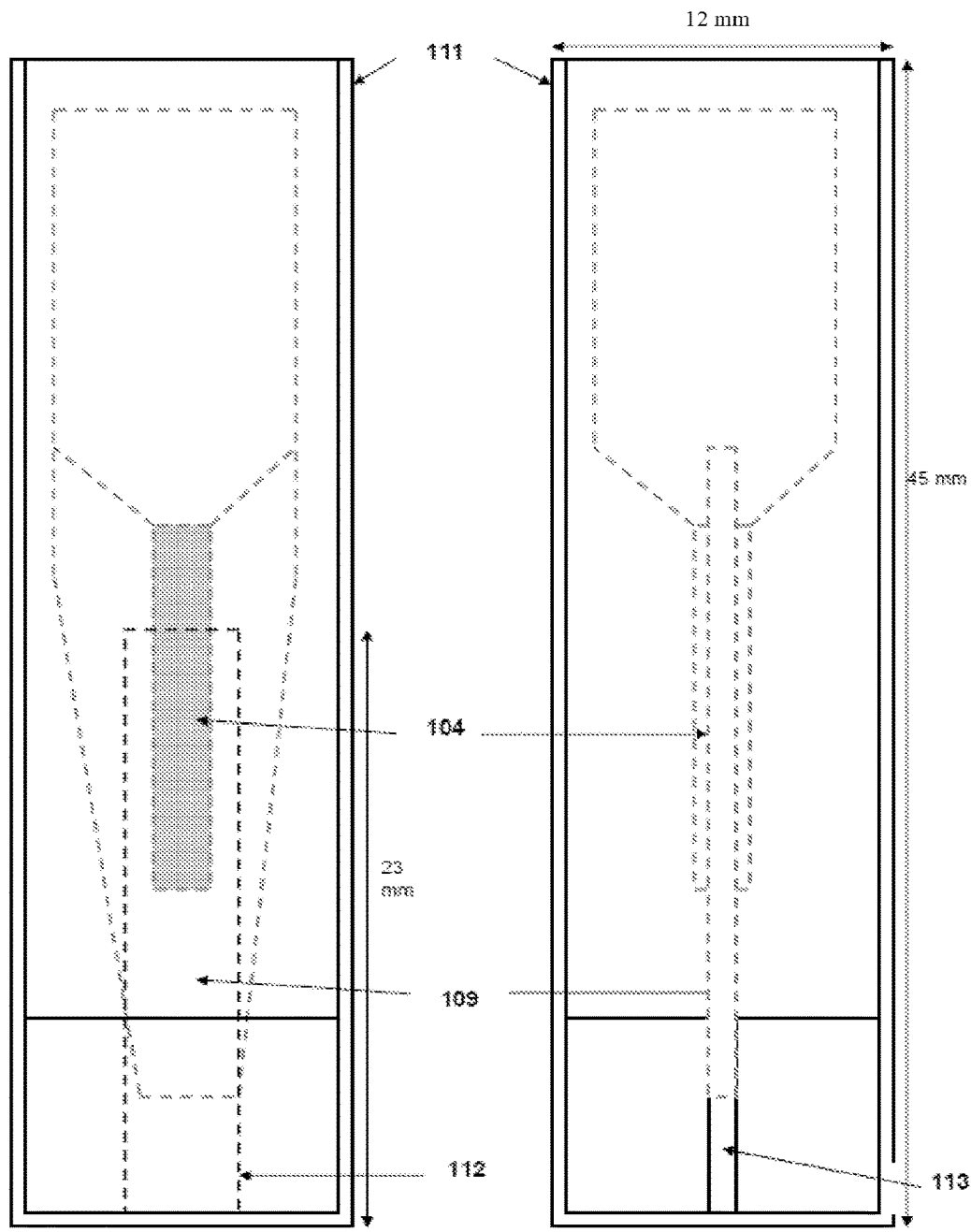
FIG. 4 depicts, in accordance with an embodiment herein, an insert cuvette 111 design as an add on to permit an insert read-out in a standard spectrophotometer. The cuvette, in one embodiment, may include a cuvette optical window 112. In accordance with another embodiment, the design may also include a mounting slot 113 to capture and orient the support fin 109 of the insert. In another embodiment, the add-on can enable read-out in a standard microplate reader.
Figure 5:
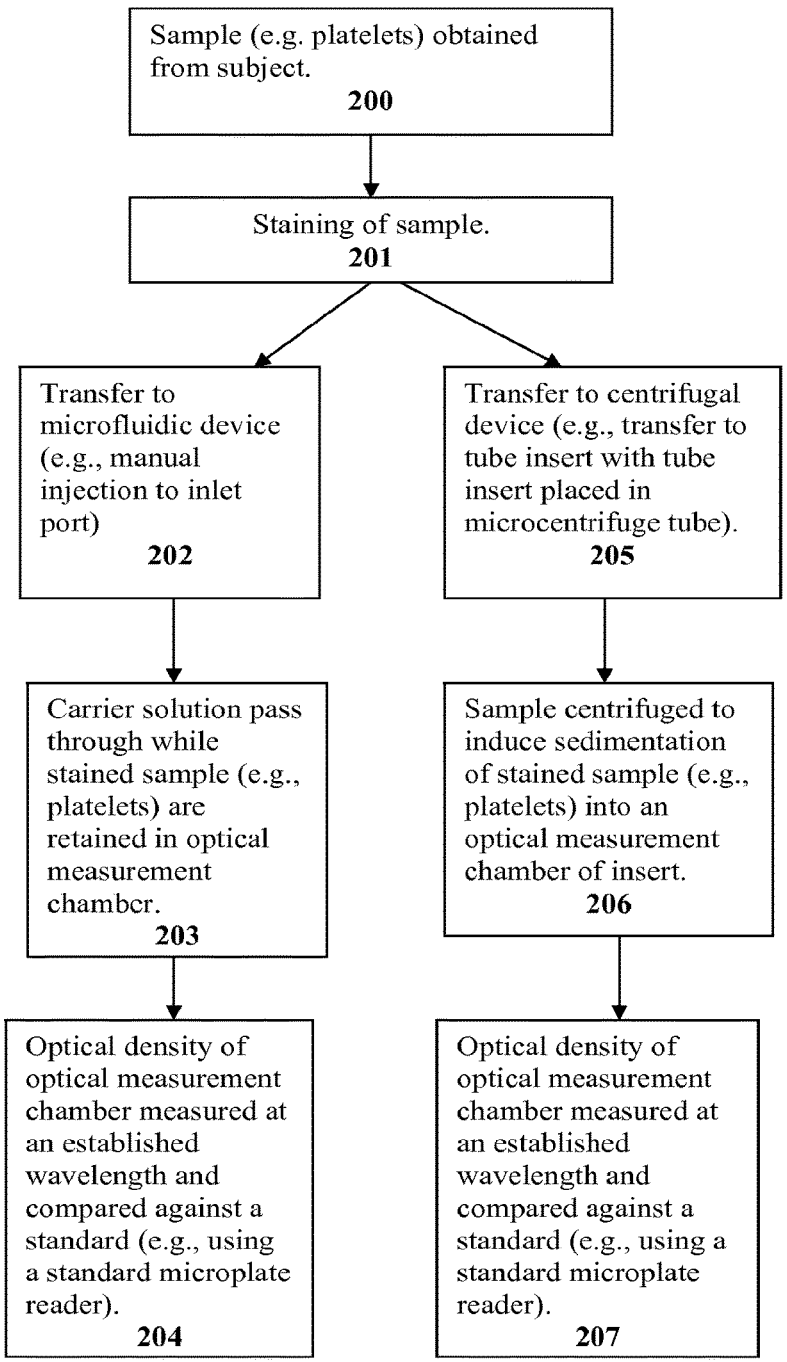
FIG. 5 depicts, in accordance with an embodiment herein, a flow chart of the overall method of quantification of a target moiety from a sample. In one embodiment, the sample may be obtained from the subject 200, followed by staining of the sample 201, then transfer to an microfluidic device 202, where the carrier solution may pass through while stained sample are retained 203, and then finally measuring the optical density and comparing the density to a standard 204. In another embodiment, the sample may be obtained from the subject 200, followed by staining of the sample 201, then transfer to a centrifugal device 205, centrifuged to induce sedimentation of stained sample 206, and then finally measuring the optical density and comparing the density to a standard 207.

Next, the optical density of the optical measurement chamber is measured at an established wavelength (e.g., 330 nm) and the result compared against a tabled value, or in concert with an included standard reference material. This measurement can be achieved, for example, by providing a manufactured plate or frame with the dimensions of a standard microplate (e.g., 96-well microplate), with the measurement chamber aligned with standard coordinates of a multiwell microplate by way of providing for the insertion of the tube insert into the frame. Thus, in any standard microplate reader, the user may select the specified well coordinates and specified wavelength as they are accustomed, and perform measurement. Another embodiment may incorporate a frame with the dimensions of a standard spectrophotometer cuvette (as shown in FIG. 4 herein), such that the measurement chamber aligned with the standard beam of a spectrophotometer upon insertion. In designs targeting measurement in a spectrophotometer or spectrophotometric microplate reader, spectrophotometric measurement at designated wavelengths is used as a proxy for densitometric measurement. Alternate wavelengths could be designated, and may or may not incorporate various correction factors, for use in non-monochromator-equipped spectrophotometric devices or when the designated wavelength cannot be otherwise used. Another embodiment may incorporate similar microfluidics design characteristics but enabling direct measurement in an optical densitometer. Each described embodiment would be equally valid and each could be provided as a kit targeted to the user's available device (e.g., "diagnostic kit for microplate readers", "diagnostic kit for spectrophotometers").

Example 8

Assay Optimization

Optimization of assays described herein may include 1) increasing signal-to-noise (reducing background, increasing sensitivity of measurement), 2) reducing costs (discarding redundant or unnecessary chemical additions), and 3) reducing time (speeding the reaction rate).

a. Reaction Linearity Toward Optimizing Staining Substrate and Time.

One critical difference between the application of DAB staining for localization of an enzyme and DAB staining for quantification of enzyme activity is the intensity to which the stain is driven. For any reliable quantification, such as in routine tissue histochemical assessments, the degree of DAB staining is held to a nonsaturating level. In contrast, many investigators maximize DAB staining to merely mark the presence of enzyme, akin to immunological techniques. Use of DAB as described herein enables its use as a continuous and quantitative, not merely a qualitative, marker; the densitometric results obtained could be linearly converted to enzymatic turnover (i.e., for example, moles of cytochrome c enzymatically reduced). Based on this premise, the assay may be tested for linearity of reaction with time, after any significant modifications to the staining parameters. One may seek to maximize signal without saturating; any "plateauing" or reduction of slope of the optical density over time will indicate saturation, and staining time will be scaled back. Cobalt chloride or other metals for intensification may also be tested as a DAB intensifier and incorporated into the protocol if it shortens staining time while maintaining/increasing signal and linearity of optical density with time.

b. Cell Permeabilization.

Histochemical staining with DAB is intensified through the use of DMSO, allowing increased cell permeability while maintaining membrane integrity. One may assess whether DMSO is required and if increasing DMSO during staining allows for shorter incubation times. Linearity of the reaction can also be assessed as above after such changes.

c. Enzyme Specificity.

This may be tested through specific Cytochrome c Oxidase inhibition with potassium cyanide (KCN). KCN is added simultaneous to the DAB in comparison assays and any residual DAB reactivity is considered background, nonspecific activity.

Example 9

Alternatives and Modifications to Design a. Internal Control Assay for Cell Number or Content.

If uniform cell packing density cannot be reliably achieved, one may also use, in conjunction with various embodiments of the device, a secondary assay to be applied simultaneously, for measurement of mitochondrial content or similar variables. The choices are numerous. Histochemical staining for succinate dehydrogenase is a logical choice, as the combination of succinate dehydrogenase/cytochrome c oxidase staining is often used in the determination of mitochondrial disease in muscle fibers. Succinase dehydrogenase is typically stained with nitroblue tetrazolium, which yields a blue stain, which may be able to spectrophotometrically distinguish from the brown diaminobenzidine reaction generated from cytochrome c oxidase. However, another choice would be another modality, such as fluorescence or luminescence, that would not interfere with the overall optical density of the preparation. Mitotracker Green FM (Invitrogen), for instance, may be employed reliably in this application. It can be quickly applied to cells in suspension, where it has been found that it stains platelets generally (likely due to the dense platelet internal membrane system), and thus could potentially provide a cell density measure. In other cell types, it is more likely to fluoresce only in mitochondria, and thus provide a reasonable mitochondrial density measure. These are but two examples considered, but if cell density is insufficient as a control, one could expect to be able to substitute another control in due course without any extensive delay.

b. Internal Control Assay for Staining Intensity.

If one is able to rely on a single staining modality (e.g., DAB), one still must consider the variability in staining outcome due, in most circumstances, to operator error. Incorrect incubation temperature is likely the most common error that would not necessarily lead to absolute failure of the assay and thus quick detection of incorrect results. While the extremes of the range of possible optical density values can be easily ruled out as errors (i.e., very light stain=low temperature; very dark stain=high temperature), milder errors could result in false negatives or false positives. Therefore, one might assess the true temperature sensitivity of the assay to allow for correction (to which incubator/water bath temperature logs could be applied). Additionally, one could include a temperature-sensitive artificial reactant (e.g., peroxidase contained within a permeable matrix) that could be stained side-by-side with the patient samples, either as an indicator of proper conditions, or as an internal correction factor for the assay results. This would, however, increase the complexity and cost of the assay.

Example 10

Histochemical Measurement of Cytochrome C Oxidase Activity Using 96-Well Plates 10 mL whole blood is drawn from a test subject into a centrifuge tube. The blood is centrifuged at 300 RCF for 15', then the PRP (platelet-rich plasma) layer is aspirated to 15 mL tube(s).

| Preparation of ACD Anticoagulant | |
|---|---|
| Step No. | Action |
| 1 | Dissolve 1.32 g of sodium citrate in 85 ml of distilled water. |
| 2 | Dissolve 0.48 g of citric acid in the solution from step 1. |
| 3 | Dissolve 1.47 g of dextrose in the solution from step 2. |
| 4 | Add distilled water to 100 ml. |
| 5 | Filter sterilize through 0.2 um filter. |

The PRP is acidified to pH 6.5 by initially adding 300 μL ACD, then adding the ACD dropwise while checking the pH of the PRP. Next, the PRP is diluted to 5 mL with Phosphate Buffered Saline (PBS). The PRP is then centrifuged at 500 RCF for 10' at room temperature. The supernatant is then transferred to a new 15 mL tube, and the pellet is discarded.

The supernatant is centrifuged at 2000 RCF for 10' to pellet the platelets, which are then resuspended in 300 μL/8 ml blood draw of Modified Tyrode's Buffer prepared as follows:

| Preparation of Tyrode's buffer | |
|---|---|
| Step No. | Action |
| 1 | Dissolve 0.8 g of sodium chloride in 85 ml of distilled water. |
| 2 | Dissolve 0.02 g of potassium chloride in the solution from step 1. |
| 3 | Dissolve 0.02 g of calcium chloride in the solution from step 2. |
| 4 | Dissolve 0.01 g of $MgCl_2 \cdot 6H_2O$ in the solution from step 3. |
| 5 | Dissolve 0.005 g of $NaH_2 PO_4$ in the solution from step 4. |
| 6 | Dissolve 0.1 g of $NaHCO_3$ in the solution from step 5. |
| 7 | Dissolve 0.1 g of glucose in the solution from step 6. |
| 8 | Add distilled water to 100 ml. |
| 9 | Filter sterilize through 0.2 um filter. |

The staining solutions (at 2×) are prepared as follows:

| Preparation of 2X Staining solutions | |
|---|---|
| Step No. | Action |
| 1 | Measure 8 mL of 20 mM PBS. |
| 2 | Dissolve 0.0012 g of cytochrome c in the liquid from step 1. |
| 3 | Add 40 μL dimethyl sulfoxide (DMSO) to the solution from step 2; mix well. This solution will be used for the control reactions. |
| 4 | To 4 mL of the solution from step 3 is added 0.004 g diaminobenzidine (DAB); mix well. |

The reaction staining solutions are then heated to 37 C. Platelets in Tyrode's are added to tubes containing an equivalent volume of 2× reaction staining solution. The tubes are closed and incubated for 1 hour in a 37 C water bath. The tubes are then centrifuged at 1600 RCF for 10' at room temperature.

The resulting pellets are resuspended and 40 μl is transferred to the round-bottom microplate wells in a 96-well plate. The microplates are refrigerated and the individual wells are allowed to sediment overnight.

Next, the OD is measured at the determined wavelength (e.g., 330 nm) and the result compared against a tabled value.

Example 11

Histochemical Measurement of Cytochrome C Oxidase Activity Using Microfilter Devices 8.5 mL whole blood is drawn from a test subject into a centrifuge tube. The tube is centrifuged at 300 RCF for 15', then the PRP (platelet-rich plasma) layer is aspirated to a 15 mL tube.

| Preparation of ACD Anticoagulant | |
|---|---|
| Step No. | Action |
| 1 | Dissolve 1.32 g of sodium citrate in 85 ml of distilled water. |
| 2 | Dissolve 0.48 g of citric acid in the solution from step 1. |
| 3 | Dissolve 1.47 g of dextrose in the solution from step 2. |
| 4 | Add distilled water to 100 ml. |
| 5 | Filter sterilize through 0.2 um filter. |

The PRP is acidified to pH 6.5 by initially adding 300 μL of ACD, then adding the ACD dropwise while checking the pH of the PRP. Next, the PRP is diluted to 5 mL with Phosphate Buffered Saline (PBS). The PRP is then centrifuged at 600 RCF for 10' at room temperature. The supernatant is then transferred to a new 15 mL tube, and the pellet is discarded.

The supernatant is centrifuged at 2000 RCF for 10' to pellet the platelets, which are then resuspended in 300 μL/8 ml blood draw of Modified Tyrode's Buffer prepared as follows:

| Preparation of Modified Tyrode's Buffer | |
|---|---|
| Step No. | Action |
| 1 | Dissolve 0.8 g of NaCl in 85 ml of distilled water. |
| 2 | Dissolve 0.02 g of KCl in the solution from step 1. |
| 3 | Dissolve 0.02 g of $CaCl_2$ in the solution from step 2. |
| 4 | Dissolve 0.01 g of $MgCl_2 \cdot 6H_2O$ in the solution from step 3. |
| 5 | Dissolve 0.005 g of $NaH_2 PO_4$ in the solution from step 4. |
| 6 | Dissolve 0.1 g of $NaHCO_3$ in the solution from step 5. |
| 7 | Dissolve 0.1 g of glucose in the solution from step 6. |
| 8 | Add distilled water to 100 ml. |
| 9 | Filter sterilize through 0.2 um filter. |

The staining solutions (at 2×) are prepared as follows:

| Preparation of 2X Staining solutions | |
|---|---|
| Step No. | Action |
| 1 | Measure 8 mL of 20 mM PBS. |
| 2 | Dissolve 0.0012 g of cytochrome c in the liquid from step 1. |
| 3 | Add 40 μL dimethyl sulfoxide (DMSO) to the solution from step 2; mix well. This solution will be used for the control reactions. |
| 4 | To 4 mL of the solution from step 3 is added 0.004 g diaminobenzidine (DAB); mix well. |

The reaction staining solution is then heated to 37 C.

Platelets in Tyrode's are added to tubes containing an equivalent volume of 2× reaction staining solution. The tubes are closed and incubated for 1 hour in a 37 C water bath. The tubes are then centrifuged at 1600 RCF for 10' at room temperature.

The resulting pellets are resuspended and 40 μl is transferred to a microfilter device as described previously. The 40 μl is added to the device's fill port.

Next, the OD is measured at the determined wavelength (e.g., 330 nm) and the result compared against a tabled value.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

1. P. Connolly, *Biosens. Bioelectron.*, 1995, 10, 1-6.
2. D. Figeys and D. Pinto, *Anal. Chem.*, 2000, 72, 330A-335A.
3. L. J. Kricka, *Clin. Chim. Acta*, 2001, 307, 219-223.
4. J. Tudos, G. A. J. Besselink and R. B. M. Schasfoort, *Lab Chip*, 2001, 1, 83-95.
5. T. H. Schulte, R. L. Bardell and B. H. Weigl, *Clin. Chim. Acta*, 2002, 321, 1-10.
6. D. Erickson and D. Li, *Anal. Chan. Acta*, 2004, 507, 11-26.
7. P. H. Sonksen, S. L. Judd and C. Lowy, *Lancet*, 1978, Apr. 8, 729.
8. S. Walford, E. A. M. Gale, S. P. Allison and R. B. Tattersall, *Lancet*, 1978, Apr. 8, 732-735.
9. D. D. Cunningham, *Anal. Chim. Acta*, 2001, 429, 1-18.
10. J. Lichtenberg, N. F. de Rooij and E. Verpoorte, *Talanta*, 2002, 56, 233-266.
11. J. P. Brody, T. D. Osborn, F. K. Forster and P. Yager, *Sens. Actuators A*, 1996, 54, 704-708.
12. P. Wilding, L. J. Kricka, J. Cheng, G. Hvichia, M. A. Shoffner and P. Fortina, *Anal. Biochem.*, 1998, 257, 95-100.
13. D. C. Duffy, H. L. Gillis, J. Lin, N. F. Sheppard and G. J. Kellogg, *Anal. Chem.*, 1999, 71, 4669-4678.
14. T. Crowley and V. Pizziconi, *Lab Chip*, 2005, 5, 922-929.

The invention claimed is:

1. A method of processing a liquid sample from a subject, the method comprising the steps of:
    obtaining a liquid sample from the subject;
    adding a reagent to the liquid sample;
    centrifuging the liquid sample to obtain platelet-rich plasma (PRP) fraction comprising unlysed platelets;
    combining the PRP fraction with a staining solution;
    concentrating the stained PRP fraction comprising unlysed platelets within a device comprising an optical measurement chamber; and
    quantifying an amount or activity of a mitochondrial protein within the concentrated PRP fraction comprising unlysed platelets from the subject.

2. The method of claim 1, wherein the reagent comprises an anticoagulant.

3. The method of claim 2, wherein the anticoagulant comprises acid citrate dextrose.

4. The method of claim 1, wherein concentrating the stained PRP fraction comprises centrifuging the stained PRP fraction within the device.

5. The method of claim 1, wherein the mitochondrial protein comprises a mitochondrial electron transport chain enzyme.

6. The method of claim 5, wherein the mitochondrial electron transport chain enzyme comprises cytochrome oxidase.

* * * * *